US005674236A

United States Patent [19]
Baugh

[11] Patent Number: 5,674,236
[45] Date of Patent: Oct. 7, 1997

[54] LANCET FOR CAPILLARY PUNCTURE BLOOD SAMPLES

[75] Inventor: Robert F. Baugh, Parker, Colo.

[73] Assignee: Medtronic, Inc., Minneapolis, Minn.

[21] Appl. No.: 640,276

[22] Filed: Apr. 30, 1996

[51] Int. Cl.⁶ .................................................. A61B 17/00
[52] U.S. Cl. ........................................... 606/181; 604/266
[58] Field of Search .................................. 604/265, 266; 606/181–183; 128/770

[56] References Cited

U.S. PATENT DOCUMENTS

| 5,029,583 | 7/1991 | Meserol et al. | 606/182 |
| 5,167,960 | 12/1992 | Ito et al. | 604/266 |
| 5,182,317 | 1/1993 | Winters et al. | 604/266 |
| 5,275,953 | 1/1994 | Bull | 128/770 |
| 5,492,763 | 2/1996 | Barry et al. | 604/265 |

*Primary Examiner*—William Lewis

[57] ABSTRACT

A lancet for obtaining a drop of blood by capillary puncture is formed by a needle having a coating thereon of a composition which precludes contact clotting activation of the blood sample.

3 Claims, No Drawings

LANCET FOR CAPILLARY PUNCTURE BLOOD SAMPLES

BACKGROUND OF THE INVENTION

1. Field of the Invention

The present invention relates to lancets or needles for obtaining blood samples by capillary puncture.

2. Description of the Prior Art

Lancets or needles have been widely used for puncturing the skin in order to obtain drops of blood for testing purposes. The lancet is generally a spring-loaded needle which is injected into a finger tip by placing the needle holder against the skin from which blood is to be drawn and pressing a release button. The trauma of such needle injection may release tissue juices and the like into the emerging blood and thus modify the blood coagulation characteristics.

OBJECTS OF THE INVENTION

It is the principal object of the present invention to reduce the trauma resulting from skin puncture by a lancet or needle for obtaining blood samples. A related object is to reduce the trauma resulting from capillary puncture and thereby prevent artificial activation of blood emerging from the puncture site.

A further object of the present invention is to provide a lancet or needle which produces a drop of blood suitable for diagnostic coagulation tests.

SUMMARY OF THE INVENTION

In accordance with the foregoing objects, the present invention is embodied in a lancet or needle for obtaining a drop of blood by capillary puncture. The blood is obtained principally for clotting analysis. The lancet is formed by a needle having a coating thereon of a composition which precludes contact clotting activation of the blood sample. The coating is intended to preclude fibrinolysis and platelet activation of the blood sample. The composition includes a blood platelet inhibitor, a prostacyclin analog and a monoclonal antibody to thromboplastin, and particularly includes aprotinin.

DESCRIPTION OF THE PREFERRED EMBODIMENT

In accordance with the present invention, an improved lancet or needle is provided for use in obtaining blood samples by capillary puncture of the skin. In order to prevent or reduce the introduction of coagulation factors into the drop of blood emerging from the puncture site, the lancet or needle is coated with one or more concentrations or reagents which inhibit systemic contact activation of the blood components and thereby block contact activation in a blood drop sample.

One such coating material is aprotinin, a serine protease inhibitor which is isolated from bovine lungs and is used to reduce post surgical blood loss in bypass surgery. By coating the lancet or needle with aprotinin, systemic contact activation would be blocked.

Additionally, the lancet could also be coated with any of several different antiplatelet activation compounds which would prevent platelet activation of the blood emerging from the wound as a result of the puncture.

Further, the tissue factor or thromboplastin in the puncture site could be neutralized using a monoclonal antibody to thromboplastin as a part of the lancet or needle coating.

In practice the lancet or needle is dipped into a solution of one or more of the above three agents and the composition allowed to dry on the needle thereby providing an effective coating on the needle for the above purposes.

Additionally, a bacteriostatic or antibacterial agent can be included in the coating composition. Other materials could be utilized such as prostacyclin for inhibiting platelets and Reopro or an RGD peptide could be used to block platelet activation. Aprotinin further is known as a good inhibitor of fibrinolysis and thus should inhibit any fibrinolysis at the puncture site.

The benefit of the coated lancet needle is that it would insure obtaining a good blood sample for use in point of care diagnostic coagulation testing where the sample is obtained by way of a finger prick. This allows a wide variety of coagulation tests to be performed on blood obtained by capillary puncture.

I claim:

1. A lancet for obtaining a drop of blood for analysis by capillary puncture comprising a needle having a coating thereon of a composition which precludes contact activation, platelet activation, and fibrinolysis of a blood sample obtained by capillary puncture.

2. A lancet for obtaining blood samples by capillary puncture comprising a lancet and a coating on the surface of said lancet of a composition including a blood platelet inhibitor, a prostacyclin analog and a monoclonal antibody to thromboplastin.

3. A lancet as defined in claim 2 wherein said composition includes aprotinin.

* * * * *